(12) United States Patent
Adiga et al.

(10) Patent No.: US 7,834,225 B1
(45) Date of Patent: Nov. 16, 2010

(54) METHOD AND DEVICE FOR SEPARATION OF LIQUID MIXTURES WITHOUT THERMAL DISTILLATION

(75) Inventors: Kayyani C. Adiga, Macon, GA (US); Rajani Adiga, Macon, GA (US)

(73) Assignee: Nanomist Systems, LLC, Macon, GA (US)

( * ) Notice: Subject to any disclaimer, the term of this patent is extended or adjusted under 35 U.S.C. 154(b) by 681 days.

(21) Appl. No.: 11/683,255

(22) Filed: Mar. 7, 2007

Related U.S. Application Data (60) Provisional application No. 60/767,168, filed on Mar. 7, 2006.

(51) Int. Cl.
*C07C 29/76* (2006.01)

(52) U.S. Cl. .................. 568/913; 568/918; 210/748

(58) Field of Classification Search ............. 210/748; 568/913, 918
See application file for complete search history.

(56) References Cited

OTHER PUBLICATIONS

Suzuki et al. {World Congress of Chemical Engineering, 7th, Glasgow, United Kingdom, Jul. 10-14, 2005, 86845/1-86845/10}.*

* cited by examiner

*Primary Examiner*—Elvis O Price
(74) *Attorney, Agent, or Firm*—Brian D. Bellamy (57) ABSTRACT

A method and device is presented for separating liquid mixtures using ultrasonic atomization and without subjecting the mixture to heat or thermal distillation. The process of ultrasonic separation does not involve liquid heating and saves up to 75% of the energy required as compared to thermal distillation. The method involves high throughput fixed bed atomizers with a specially designed carrier gas flow for aerosolization, extraction, and transport of mist. The mist richer in the desired component is then collected and condensed by electrostatic or other de-misting means. Repeated processes can achieve high separation efficiency. The efficiency of separation can be controlled by varying the ultrasonic frequency, power, and number of arrays, liquid surface tension and interfacial tension of mixtures.

29 Claims, 6 Drawing Sheets

Distillation Energy was taken from Purdue University Report

Fig. 7

METHOD AND DEVICE FOR SEPARATION OF LIQUID MIXTURES WITHOUT THERMAL DISTILLATION

Applicants claim priority benefit of the U.S. Provisional Patent Application No. 60/767,168 filed on Mar. 7, 2006.

BACKGROUND OF THE INVENTION

This invention relates to the separation of liquid mixtures without subjecting the mixture to thermal distillation.

Thermal distillation is widely used for separating miscible liquid components with different boiling points. Thermal distillation technology is well developed and is used widely. For example, one of the huge market-driven thermal distillation applications is ethanol production, wherein alcohol is separated from a fermentation mixture by fractional distillation. Although the net energy produced in this process is low, thermal fractional distillation is the widely accepted separation method. Less common known ways of separating miscible liquid mixtures are vacuum distillation, electric field separation, and membrane separation.

Ultrasonic atomization processes have been explored for separating water and ethanol in laboratory-scale bench top experiments. Research has shown that an atomized mist becomes richer in ethanol with time as compared to the mixture of ethanol and water they started with. However, there is no prior art scalable process technology for a miscible liquid separation based on ultrasonic atomization, without using thermal distillation. The scaling issues in ultrasonic methods are extremely complex. Some of the well-recognized scaling problems come from the heating effect of ultrasonic transducers, the liquid mixing, and liquid extraction, maintaining a constant liquid level above the atomizer surface, and mist composition (liquid mass mist loading in air). As a result, prior art in ultrasonic separation is absent at the commercial scale and throughput is limited.

Typical ethanol production by thermal distillation is given here as an example. Fermentation is used to produce alcoholic beverages. Beer and wine do not contain more than around 12% alcohol, because a higher concentration kills the yeast that produce the alcohol. To make stronger drink, fractional distillation is used. Wine, beer, or fermented brews made from corn, sugar cane potatoes or other starches can be made richer in alcohol by distillation. Since ethyl alcohol boils at only 78° C., while water boils at 100° C., the alcohol will boil off, leaving the water behind. The alcohol vapors are then condensed and collected. Distillation can produce liquors that range from 40-95% ethyl alcohol. The energy for distillation based on the latent heat of vaporization of ethanol is 884 kJ/kg, without considering the heat transfer limitations (efficiency factor <1.0) in distillation. A need exists to reduce the energy required in production of ethanol and separation of liquid mixtures.

SUMMARY OF THE INVENTION

This invention provides a highly scalable ultrasonic process for separating a liquid mixture, such as ethanol and water, with different boiling points. By not subjecting the liquid mixture to heat or thermal distillation, the process is highly energy efficient. For example, the ultrasonic atomization process of the current invention requires less than 215 kJ/kg of energy for separation of a miscible liquid mixture based on the energy required to atomize ethanol liquid into 1-5 micron droplets. This is only about 25% of the energy required for separation, as compared to thermal distillation. Thus, the ultrasonic atomization process of this invention separates a more volatile liquid component from the liquid mixture at 75-80% lower energy consumption as compared to separation by thermal distillation. With respect to ethanol production, this represents a significant energy savings in view of the present oil dependence and alternative energy needs.

Separation of liquid mixtures by ultrasonic atomization does not require a liquid to heat to its boiling point, but will only subject the liquid to a high level of cavitations. Ultrasonic atomization results from compression and rarefaction waves formed within the liquid that creates enormous energy and pressure in very short time scales. A liquid reaction mixture is provided in a column in a batch or an online continuous feed process. The reaction mixture is subjected to ultrasonic atomization in which during atomization, a fountain forms above the liquid surface, and droplets form and mist discharges from the fountain. The atomization rate and efficiency directly relates to the liquid vapor pressure-boiling point of the liquid components. In particular, when water and ethanol are mixed and atomized, ethanol, being the more volatile component, atomizes more efficiently than water. The mist-phase product will be richer in ethanol, thereby separating ethanol from a reaction mixture as it is formed. The atomized mist coming out of a separation column becomes richer in more volatile components, while the liquid mixture in the column remains at ambient temperature.

An objective of the invention is to provide a non-thermal process technology to remove the adverse effect of heating found in thermal distillation processes, such as used in separating ethanol from water and a reaction mixture.

Another objective is to provide an ultrasonic atomization process for online and continuous separation of a liquid mixture into separate components, whereby, in particular, ethanol and water may be separated in a continuous process in the production of ethanol.

Another objective is to devise a method and device for collecting a mist that will provide a richer component by electrostatic means and/or a de-misting matrix, wherein the more volatile misted component is recovered.

Another objective is to devise an ultrasonic atomization process of separating components such as ethanol and water at industrial scale (many liters per minute) using large scale ultrasonic atomizer-extractors.

Another objective is to use high mist loading in a carrier gas such as 45-50% by weight using a special misting device so that the collection of mist and de-misting volume will be minimal.

Another objective is to use a specially designed carrier gas flow pattern so that the atomization fountains are not disrupted in order to maintain a high atomization rate.

Another objective is to avoid heating of the liquid mixture by heat release from the ultrasonic atomizer transducer by providing a system of separating the liquid mixture from the atomizer through a sound transparent diaphragm. A further object is to cool the atomizer disk by a flow of water that is separated from the liquid mixture by the sound transparent diaphragm.

Another objective is to separate the electronics of the transducer from the piezo crystals of the ultrasonic atomizer and cool the electronics of the atomizer separately by air or other coolants. The atomizer disk with ultrasonic wave sound producing system will be separated from the electronics that drive the resonance.

Another objective is to use pressure assisted ultrasonic nozzles as a mist production method in place of piezo crystals to initiate sound waves and sonication so that electronics will be simplified and heating of the liquid mixture by the electronics will be avoided.

Another objective is to use a surfactant and/or additive to widen the difference in vapor-pressure boiling point difference between components of the miscible liquid mixture so that separation efficiency will increase.

Another objective is to separate azeotropes where thermal distillation cannot separate the mixture anymore. At those compositions, azeotropes boil with constant compositions. Chemicals or membrane methods are generally used for further separation. The ultrasonic method, because of the cavitation process, can separate such mixtures without using chemicals, or membranes.

Another objective is to extract and transport extremely fine mist with extremely low momentum so that an electrostatic or any other de-misting, mist collecting and coalescing process can be used to recover ethanol or volatile liquid component from the misting process.

Yet another objective is to enrich the separated component by repeated atomization and condensing processes, similar to fractional distillation used in a thermal distillation process. The collected condensate from one batch of ultrasonic atomization is taken to step two and repeated until desired condensate concentration is obtained.

These and other objectives will be apparent to those skilled in the art in view of the present description of the invention, and the scope of the invention should be interpreted in accordance with the claims.

DETAILED DESCRIPTION OF THE INVENTION

The present invention is applicable to generally liquid mixtures comprising two or more miscible or immiscible components. However, the invention is particularly applicable to the industrial process for separation of miscible liquid mixtures, and, in particular, applicable to producing ethanol from an ethanol and water mixture during a fermentation process using an ultrasonic atomization process. The process provides separation of a volatile liquid component, such as ethanol, at an industrial scale of several liters per minute using large scale ultrasonic atomizer-extractors. The present invention is not restricted to application to ethanol mixtures but may be applied to the separation of any multi-component liquids with differing volatilities. The particular processes for removing ethanol from liquid fermentation mixtures will be discussed herein as an example of a particularly beneficial application of the invention.

The process technology provides for the online removal of ethanol concentration levels at ambient temperature by atomization of the liquid mixture without using pressure nozzles or thermal distillation. Ethanol is removed from a liquid mixture using high throughput ultrasonic atomization and a misting device in which high mist loading (up to 45-50% wt) is achieved using a carrier gas in combination with a specifically configured misting device so that the collection of mist and de-misting volume will be minimal. While a wide range of frequencies may be used, a frequency of ultrasonic vibrator of 2.4 MHZ is effective to generate an appropriate high volume mist. The generated mist is collected by suitable means, such as by electrostatic voltage of $-1,000$ V to $-10,000$V, causing the misted component to condense and coagulate back into a liquid phase. The ethanol component of the liquid mixture is separated by collecting the atomized droplets from the outlet stream coming out of ethanol traps installed at the top of the fermentation reactor.

Figure 1:
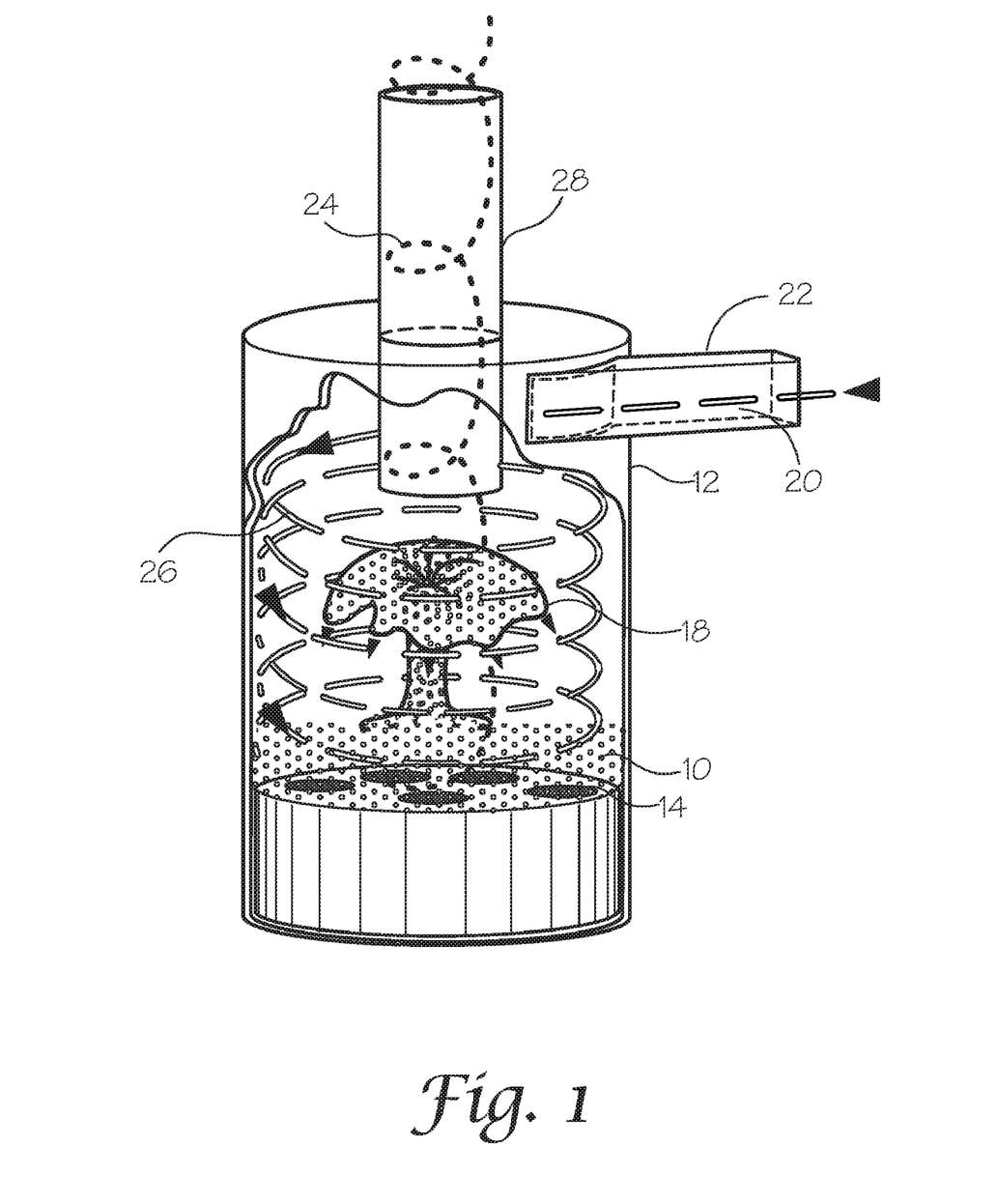
FIG. 1 is a schematic perspective view of a model ultrasonic liquid mixture separator in accordance with one possible embodiment of the present invention.
Figure 2:
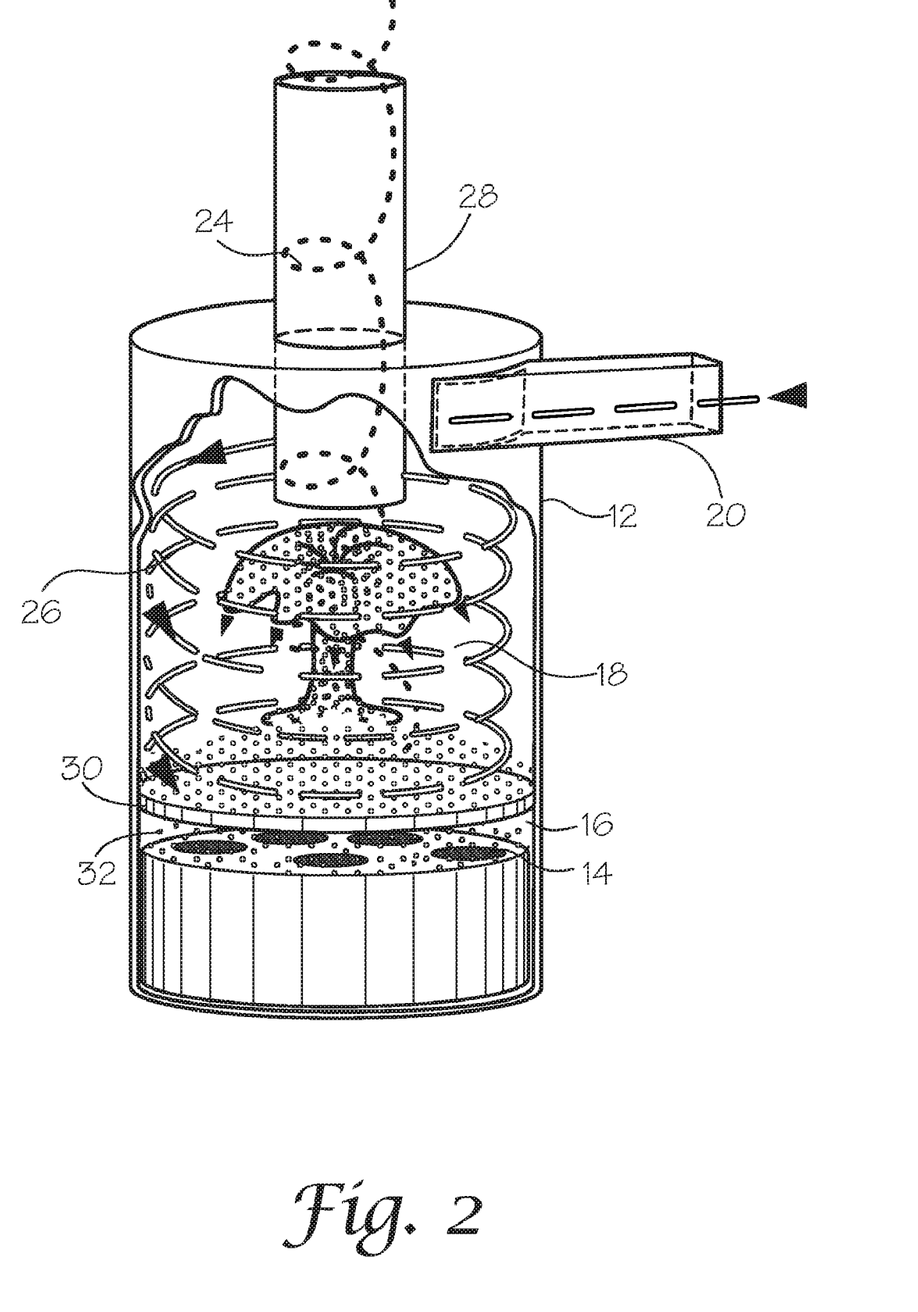
FIG. 2 is a schematic perspective view of a model of an ultrasonic liquid mixture separator with means for physical separation of an ultrasonic atomizer.

FIG. 1 shows an example of ultrasonic separator geometry and specifications. The liquid mixture 10 to be separated is contained in a separator column 12. The liquid mixture 10 may be supplied continuously or could be supplied in an ongoing batch process. As shown in FIG. 1, ultrasonic atomizer transducers 14 are immersed inside the liquid mixture 10. The transducer 14 is also called atomizing disk. In the embodiment of FIG. 2, the ultrasonic atomizer transducers 14 may be contained within a separated compartment 16 in order to avoid heat transfer from the transducers 14 to the liquid mixture 10 and to avoid direct contact of the transducers with the liquid mixture.

During atomization, the liquid mixture 10 forms a fountain 18, as shown in FIG. 1. A fine mist comes out of the fountain 18, and a carrier gas 20 (generally air) enters the column 12 through the tangential inlet 22, swirls helically downwards, and picks up mist without disrupting the fountain process. The swirling carrier gas aerosolizes the drops immediately into a pseudo-gaseous aerosolized liquid 24 so that the droplets do not coalesce and form liquid. Aerosolizing the mist controls and minimizes undesirable coalescing and liquid formation during the process. In particular, the specially designed helical carrier gas flow pattern 26 does not disrupt the atomization fountains 18, thereby maintaining the high atomization rate of the liquid mixture 10. After aerosolizing the mist to form an aerosol liquid 24 of mist, the aerosol 24 enters a tube 28, which is referred to as a central vortex finder. The tube 28 is centrally situated within the column 12 and provides and outlet from the column chamber for the aerosol to transport from the chamber to a collection means. The aerosolized liquid 24 of mist is thus transported outside of the column 12 for collection and separation of the volatile liquid component of the liquid mixture 10. The ratio of liquid mist to carrier gas 20 can be varied in order obtain an aerosol 24 highly concentrated in liquid mist droplets. Upon transporting out of the column 12, the aerosol 24 of mist is passed through a de-misting system, such as an electrostatic condenser as an additional step to separate the volatile liquid component from the liquid mixture 10. The momentum of the carrier gas 20 is controlled to transport the extremely fine mist with an extremely low momentum so that an electrostatic or any other de-misting, mist collecting and coalescing process can be used to recover ethanol from the misting process.

Figure 3:
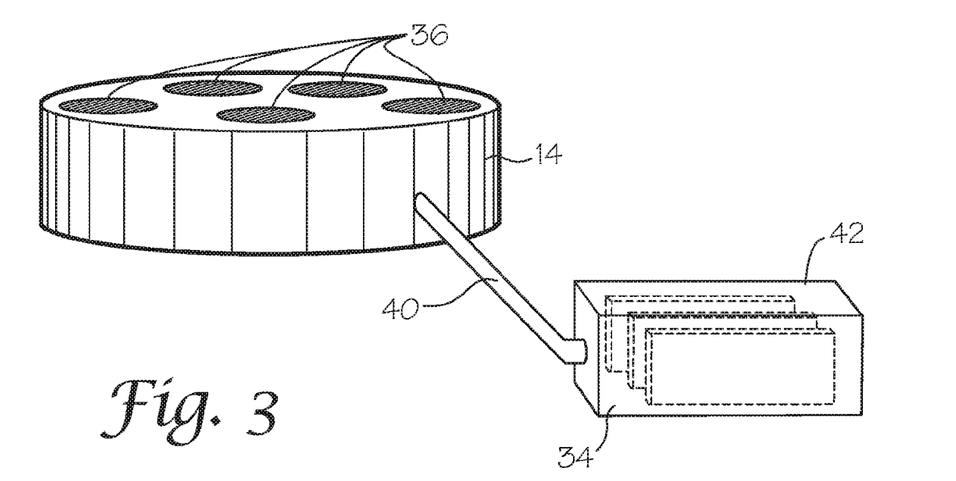
FIG. 3 is a schematic illustration of a ultrasonic atomizer system in relation to the invention having atomizer disks separated from an electronic driver circuit.
Figure 4:
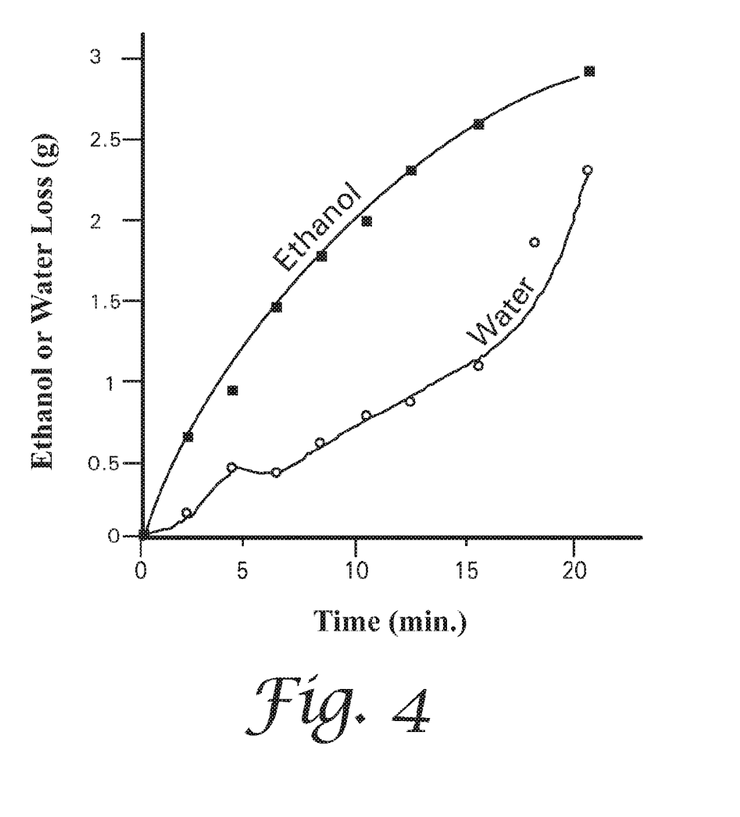
FIG. 4 is a graph showing ethanol and water loss during atomization of a liquid mixture in accordance with the present invention.

Generally, the transducer 14 (atomizing disk) releases heat during its operation. Without additional measures, this heat will transfer to the liquid mixture 10 potentially causing adverse effects on the separation process. Measures for avoiding deleterious transfer of heat from the transducer 14 are illustrated in FIGS. 2 and 3. One means, shown in FIG. 2, separates the atomizer disk 14 assembly from the liquid mixture using a sound transparent diaphragm 30 that allows sound waves to pass through. Thus, a non-contact atomizer system is provided in relation to the liquid mixture 10. An additional cooling liquid 32 is provided surrounding the atomizer system transducer 14, which does not directly contact the liquid reaction mixture 10. The transducers 14 may be separately cooled continuously by water or any other suitable cooling liquids, whereby the atomizing system will not heat up the liquid mixture 10. Physical separation of the mixture from the transducers 14, as in FIG. 2, provides additional advantage and versatility in that the liquid reaction mixtures 10 may otherwise be corrosive to the material of ultrasonic transducers 14.

In another alternative embodiment, the electronic driver boards 34 are separated from the related atomizer piezo disks 36 or atomizer jets for cooling of the ultrasonic transducer 14, as illustrated in FIG. 3. Separation of the electronic drivers 34 from the transducer 14 removes the heat produced by these driver boards and, therefore, the atomizer piezo disks 36 or atomizer jets remain cool. Since the electronic driver boards 34 that were previously embedded with the transducer 14 are separated, the atomizing piezo disks 36 or jets may be placed inside the liquid mixture container column 12 without adversely heating the liquid mixture 10. Heat generating electronics in contact with the liquid mixture 10 may be further minimized by adding other assistive measures. For instance, pressure assisted ultrasonic nozzles may be incorporated into the atomizer system in place of piezo crystals to initiate sound waves and sonication. Such pressure assisted nozzles may allow the electronics of the atomization system to be simplified and minimized to avoid the generation of heat by the system.

The drivers 34 that usually heat up during atomization are removed from the transducer 14 and connected through cables 40. The drivers 34 are separately mounted and cooled inside a separate container 42, which avoids the heating of the liquid mixture 10 during continuous processing. The electronics may be cooled by air or other coolants to minimize the heat generated thereby.

The ability to remove alcohol selectively from an ethanol and water liquid mixture by ultrasonic atomization is shown by the graph in FIG. 4. The liquid considered by the graph is withdrawn at a regular interval and analyzed for ethanol by gas chromatography (GC). In the example, a 50:50 wt percent mixture was taken in an ultrasonic atomizer column with 2.4 MHz frequency. As a function of time, the proportion of ethanol lost from the initial liquid mixture increases; the mist phase shows a progressive enrichment in ethanol. The graph illustrates that, as a function of time, the atomized spray coming out of the reactor is richer in ethanol as compared to water. Using this process in extraction of ethanol from a fermentation reactor removes ethanol from the liquid reaction mixture that normally would inhibits the rate of fermentation if not extracted continuously while the reaction is occurring online. The continuous extraction of ethanol from the fermenting mass takes place without an inhibiting ethanol concentration buildup in the fermentation reaction mixture. Further, the extraction of ethanol from the fermenting mass takes place without the addition of heat or energy to the reactant mixture. Because the addition of heat is not necessary and the ethanol inhibition factor is removed, the ethanol separation may be carried out online by atomization without terminating the fermentation process. Therefore, the continuous online process allows for miscible liquids to be concentrated into the more volatile component by causing a higher percentage of the more volatile component with a smaller percentage of the less volatile component to be extracted through ultrasonic atomization, extraction and collection. By these steps, the use of ultrasonic separation to obtain ethanol increases the yield and rate of production from a particular fermentation process.

As a further step, the purity of the separated component may be enriched by further processing. Similar to fractional distillation used in thermal distillation processes, the separated component may be enriched further by repeating the atomization and condensation process to create an enriched mist providing a further enriched volatile liquid component. In the ultrasonic separation process, the prior separation step continues production, while the collected condensate from the prior step of ultrasonic atomization is taken to a further step and ultrasonic atomization is repeated until the desired enrichment of the volatile liquid component and separation efficiency is obtained.

In addition to providing for a continuous online extraction of volatile liquid components, the atomization process may be used to separate azeotropes, as an alternative to using molecular sieves. In thermal distillation methods, azeotropes cannot be separated because the azeotropes boil with a constant composition. In an azeotrope consisting of two compounds X and Y, the ratio of compounds will remain exactly the same in both the vapour form of the mixture, X:Y as in the liquid phase. Therefore, the chemical composition of the azeotrope cannot be changed by simple boiling. Therefore, chemicals or membrane methods are generally used to separate azeotropes further. However, the ultrasonic method discussed herein may be used to separate the azeotropes, as the cavitation process generates a mist that is rich in the volatile component, and the volatile component of a liquid azeotropes mixture may be separated through the atomization process without using chemicals, membranes or molecular sieves.

In general, the efficiency of extraction of ethanol from an ethanol-water mixture by ultrasonic atomization depends upon the process controls discuss hereinabove, including power input to the ultrasonic atomization device. The efficiently of extraction is also dependent upon the constantly relevant factors of water concentration and temperature of the solution. Separation of ethanol from water is excellent at low power energy input, measured in Watts. In addition, separation is efficient when the liquid mixture of ethanol and water is at ambient temperatures. Whereas, at higher temperatures and higher energy input, more water is atomized along with ethanol, diluting the richness of the generated mist, making the separation process less efficient.

Using the described extraction process and device, an ethanol rich mist has been extracted, and the ethanol-water solution has been sampled and its density measured to determine ethanol concentration of the mist. Typical separation experiments completed to confirm the ethanol separated in the gas phase use the formula $$[EtOH_{g-phase}] = \left[\frac{[ETOH]_{t=t0}m_{t0} - [ETOH]_{t=tf}m_{tf}}{m_{t0} - m_{tf}}\right]_{liquid-phase}$$

Where, [ETON] is the liquid-phase concentration of ethanol in the mixture, % wt., "t" is the time in minutes or seconds, "t0" is the initial time, and "tf" is the final time. "$m_{r0}$" is the initial mass of liquid (kg) and "$m_{tf}$" is the final mass of the mixture (kg).

Figure 5:
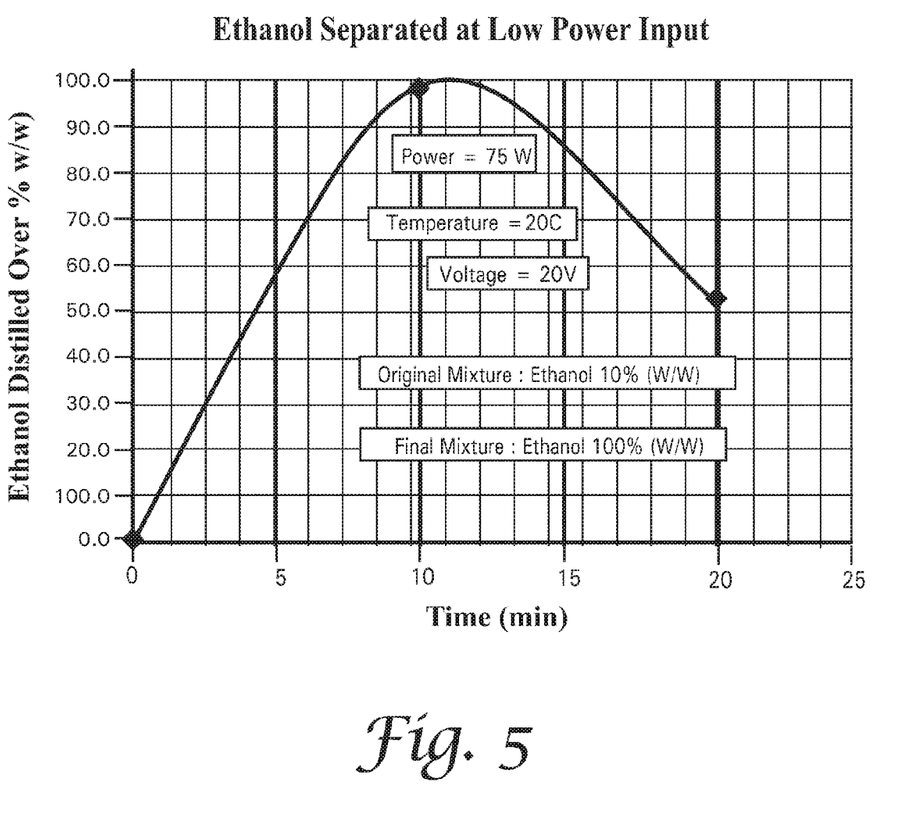
FIG. 5 is a graph showing the separation of ethanol from an ethanol-water mixture at lower power input as a function of time.
Figure 6:
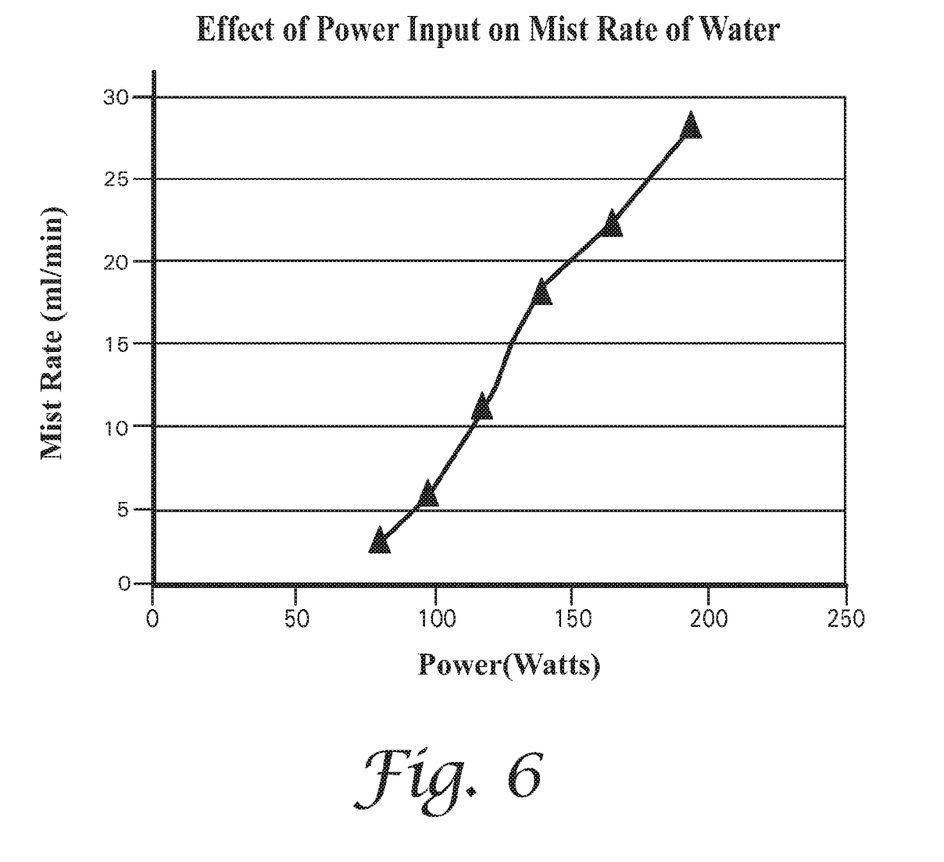
FIG. 6 is a graph showing the rate of mist production by ultrasonic atomization as a function of power input.

As seen in the graph of FIG. 5, pure ethanol can be separated at low power input, in this example 75W for 9-atomizer jets piezo disks 36. If a single atomizer jet or piezo disk is used, the power input may be as low as about 8-10 Watts for typical American Piezo Co. (APC) piezo crystals. Moreover, time is an important factor in combination with the lower power input in determining the concentration of ethanol in the mist. As seen in the example of FIG. 5, the ethanol mist collected at about 10 minutes is 100% pure ethanol. After 10 minutes, the mist includes more water as it is generated from the liquid mixture. At higher power input, the time elapsed before the production of a high percentage ethanol mist may be lower, as the production rate of mist varies as a function of power input as shown in FIG. 6. At a sufficiently high-energy input, the time factor may be reduced to a few seconds before ethanol concentration of mist reach 100%. As seen in FIG. 6, the mist output is very low where the power input is a low 75 W as in the example of FIG. 5. Whereas, as power input increases, the production rate of mist increases, but, as stated, peak ethanol concentration of the mist occurs earlier and water starts to comprise a larger portion of the mist after a shorter period of time.

High-energy input to produce a high concentration mist may be accomplished via a pulse of energy calibrated in accordance with the preferred calibrated time for production of the desired concentration of ethanol rich mist. A number of modular units may be applied to accomplish good separation using the desire pulse of energy. More particularly, a pulsed method of inputting specific levels of ultrasonic energy in bursts for a specific time may be applied, whereby a continuous series of pulses may be used to generate an alcohol/ethanol rich mist and to extract the same efficiently. The power input to the atomizer and the time-length of application may be optimized according to desired specifications for ethanol concentration and throughput.

Figure 7:
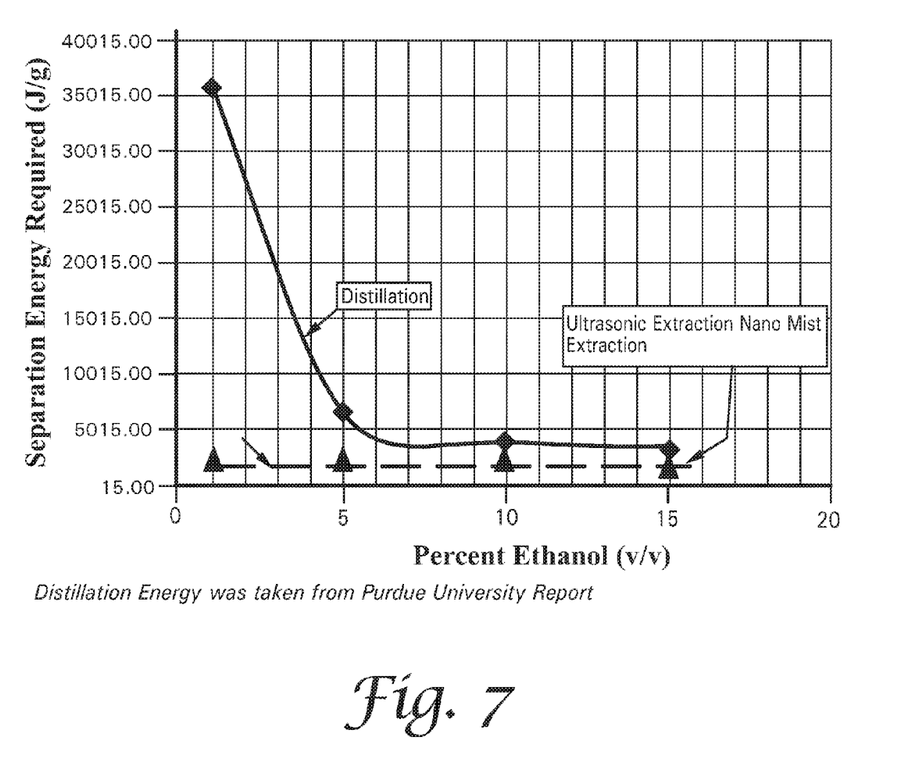
FIG. 7 is a graph showing the energy required for separation of ethanol from an ethanol-water mixture as a function of the percent ethanol in the mixture.

The graph in FIG. 7 shows a comparison of the energy required to separate ethanol by thermal distillation and by the ultrasonic methods discussed herein. The energy required by ultrasonic atomization using the procedures discussed is relatively insensitive to the water content of the ethanol-water mixture. The energy required by thermal distillation is greater than in the ultrasonic process and dependent upon the water content of the mixture because heating the mixture is required. The practical range for a fermentation process is 1-10% ethanol content in the ethanol-water mixture. The lower energy required for separation by ultrasonic atomization is particularly important with respect to liquid mixtures containing large amounts of water of about 90-99% content and having ethanol content in the 1-10% range.

Taking advantage of the lower energy required, the ultrasonic atomization process may be used to achieve a high level of separation of ethanol from water at a low cost. For example, the process of ultrasonic atomization and extraction discussed may be used to concentrate ethanol from 5-6% (v) to 14-15% (v) in the production of wine or 30-40% (v) in the production of liquor.

Several additional steps may be provided in the separation process to enhance and improve efficiency. First, varying the frequency and current input to the transducer will effect the production of mist and may be fine tuned according to preferred mist production rates. Additionally, the liquid mixture and components thereof may be manipulated to improve atomization characteristics.

For instance, surface/interfacial tension of the liquid mixture components may be varied using surfactants and other additives. The droplet diameter, d in ultrasonic atomization relates to:

$$d = C[\tau/(\rho f^2)]^{1/3}$$

Where C is a constant, $\tau$ is surface tension of liquid, $\rho$ is the liquid density and f is the frequency of the ultrasonic transducer. The droplets become smaller if the surface tension is reduced. Surfactants can reduce surface tension and interfacial tension of the mixture significantly.

Also to enhance separation of a more volatile component, the boiling point of the liquid components in the mixture may be widened. Means to widen the boiling point difference of those volatile and non-volatile components would include using additives, as well as using microemulsion techniques. In a fermentation liquid reaction mixture, forming a microemulsion of water in the presence of a surfactant would widen the gap between the boiling point of the water and ethanol. This would further assist in separating ethanol and water by an ultrasonic misting process in that the boiling point of water would be increased as much as 10-20° C. depending on the chain-length of oil added to water to make the microemulsion system.

We claim:

1. A method for separation of liquid mixtures comprising the steps of:
   supplying a reservoir of liquid mixture in a separator column;
   atomizing the liquid mixture to form a fountain producing a fine mist;
   providing a carrier gas to aerosolize the fine mist into an aerosol containing a volatile liquid; and
   collecting the aerosolized liquid to separate the volatile liquid from the liquid mixture.

2. A method for separation of liquid mixtures as in claim 1 in which said liquid mixture in supplied to the reservoir in a batch.

3. A method for separation of liquid mixtures as in claim 1 in which said liquid mixture is supplied to the reservoir continuously online to replenish the reservoir with the liquid mixture.

4. A method for separation of liquid mixtures as in claim 1 in which the aerosolized liquid is collected by an electrostatic voltage to separate the volatile liquid from the liquid mixture.

5. A method for separation of liquid mixtures as in claim 1 in which the liquid mixture includes water and ethanol and the volatile liquid is ethanol and the separator column includes a fermentation reactor.

6. A method for separation of liquid mixtures as in claim 5 in which the aerosolized liquid is collected by an ethanol trap above the fountain to separate the ethanol from the liquid mixture.

7. A method for separation of liquid mixtures as in claim 1 in which the step of providing said carrier gas to aerosolize the fine mist includes:
   directing a helical flow of the carrier gas downward in the separator column to aerosolize the mist; and
   receiving the aerosolized mist into an inner tube within the separator column and transporting the aerosolized mist through the inner tube.

8. A method for separation of liquid mixtures as in claim 1 in which the liquid mixture is atomized using an electronic transducer generating ultrasonic waves for atomization.

9. A method for separation of liquid mixtures as in claim 8 in which the electronic transducer is immersed in the liquid mixture.

10. A method for separation of liquid mixtures as in claim 8 in which the electronic transducer is separated from the liquid mixture by a diaphragm transparent to the ultrasonic waves.

11. A method for separation of liquid mixtures as in claim 10 in which the electronic transducer is cooled by a cooling liquid.

12. A method for separation of liquid mixtures as in claim 8 in which the electronic transducer is cooled by separating electronic drivers of the transducer from atomizer piezo disks or atomizing jets and removing the electronic drivers from the reservoir.

13. A method for separation of liquid mixtures as in claim 1 in which the liquid mixture has two or more liquid components each having an interfacial surface tension and including an additional step of adding an additive to change the interfacial surface tension of at least one of the liquid components of the liquid mixture.

14. A method for separation of liquid mixtures as in claim 1 in which the liquid mixture has two or more liquid components each having a boiling point and including an additional step of adding an additive or providing a microemulsion to change the boiling point of at least one of the liquid components of the liquid mixture.

15. A method for separation of liquid mixtures as in claim 1 in which the aerosolized liquid is collected and includes an additional step of condensing the volatile liquid from the aerosolized liquid to separate the volatile liquid from the liquid mixture.

16. A method for separation of liquid mixtures as in claim 5 in which the aerosolized liquid is collected and includes an additional step of condensing the ethanol from the aerosolized liquid to separate the ethanol from the liquid mixture.

17. A method for separation of liquid mixtures as in claim 1 in which a power input of 8 to 10 Watts is provided to an ultrasonic atomizer piezo disk in the step of atomizing the liquid mixture to form the fountain producing the fine mist and after atomizing the liquid mixture a predetermined time the fine mist produced comprises pure volatile liquid.

18. A method for separation of liquid mixtures as in claim 1 in which the liquid mixture is considered an azeotrope.

19. A method for separation of liquid mixtures as in claim 5 in which the aerosolized liquid is 14-15% by volume ethanol.

20. A method for separation of liquid mixtures as in claim 5 in which the aerosolized liquid is 30-40% by volume ethanol.

21. A method for separation of liquid mixtures as in claim 1 in which the liquid mixture is maintained at ambient temperature.

22. A method for separation of liquid mixtures as in claim 1 in which the liquid mixture is maintained at a temperature of between 1° and 10° C.

23. A method for separation of liquid mixtures as in claim 1 in which the step of collecting the aerosolized liquid to separate the volatile liquid from the liquid mixture forms a separated component, and the separated component is atomized, aerosolized and an enriched mist thereof is collected to provide a volatile liquid component of desired enrichment.

24. A method for separation of liquid mixtures comprising the steps of:
   supplying a reservoir of liquid mixture that includes a volatile liquid;
   atomizing the liquid mixture in a series of pulses in which an ultrasonic atomization device is provided a power input of a predetermined amount and in which each pulse continues for a predetermined time and a mist containing the volatile liquid is produced by each pulse;
   collecting the mist or the volatile liquid from the mist to extract a final liquid comprising an increased proportion of the volatile liquid than existed in the liquid mixture.

25. A method for separation of liquid mixtures as in claim 24 in which the volatile liquid is ethanol.

26. A method for separation of liquid mixtures as in claim 25 in which the liquid mixture comprises 5-6% by volume of the ethanol and the final liquid comprises 14-15% by volume of the ethanol.

27. A method for separation of liquid mixtures as in claim 25 in which the liquid mixture comprises 5-6% by volume of the ethanol and the final liquid comprises 30-40% by volume of the ethanol.

28. A method for separation of liquid mixtures as in claim 24 in which the liquid mixture is maintained at a temperature of between 1° and 10° C.

29. A method for separation of liquid mixtures as in claim 24 in which the predetermined time is 10 minutes or less depending on the power input.

* * * * *